United States Patent [19]

Tengvall et al.

[11] Patent Number: 5,045,318

[45] Date of Patent: Sep. 3, 1991

[54] ANTI-INFLAMMATORY OXIDIZING AGENT, THE PROCEDURE FOR ITS PRODUCTION AND VARIOUS APPLICATIONS

[75] Inventors: Pentti Tengvall, Linköping; Lars-Magnus Bjursten, Göteborg; Ingemar Lundström, Linköping, all of Sweden

[73] Assignee: The Institute for Applied Biotechnology, Goteborg, Sweden

[21] Appl. No.: 411,466

[22] PCT Filed: Jan. 19, 1989

[86] PCT No.: PCT/SE89/00015

§ 371 Date: Sep. 19, 1989

§ 102(e) Date: Sep. 19, 1989

[87] PCT Pub. No.: WO89/06548

PCT Pub. Date: Jul. 27, 1989

[30] Foreign Application Priority Data

Jan. 20, 1988 [SE] Sweden ............................ 8800176

[51] Int. Cl.$^5$ ...................... A61F 13/00; A61K 33/40; A61K 33/26

[52] U.S. Cl. ................................... 424/422; 424/613; 424/617; 423/598

[58] Field of Search .................. 424/422, 617, 613; 423/598

[56] References Cited

FOREIGN PATENT DOCUMENTS 791503 10/1972 Belgium .

OTHER PUBLICATIONS

Advanced Inorganic Chemistry, Cotton and Wilkinson, p. 699, 1980.

*Primary Examiner*—Thurman K. Page
*Assistant Examiner*—G. S. Kishore
*Attorney, Agent, or Firm*—Ostrolenk, Faber, Gerb & Soffen

[57] ABSTRACT

The reaction product of $H_2O_2$ and metallic titanium, a titanium peroxy radical gel, exhibits oxidizing and anti-inflammatory effects and is used, for instance, as a biocompatible oxidant, an anti-inflammatory agent or in vitro coating of an implant body. The gel-like product is produced by treating metallic titanium with $H_2O_2$.

10 Claims, No Drawings

ANTI-INFLAMMATORY OXIDIZING AGENT, THE PROCEDURE FOR ITS PRODUCTION AND VARIOUS APPLICATIONS

The present invention relates to an anti-inflammatory oxidizing agent, the procedure for its production and various applications.

The production of disinfectants from titanium salts and hydrogen peroxide is known in the art. Refer, for instance, to Belgian patent No. 791 503 describing how a hydroxy gel is first produced from titanium salt solutions and hydrogen peroxide, after which further hydrogen peroxide is added at a pH value of 7. The disinfectant effect of such solutions is substantially the same as that obtained with hydrogen peroxide solutions.

According to the invention it has now proved possible to considerably improve the effect of such agents, while at the same time obtaining a substantially transparent agent.

This is achieved according to the invention substantially in that the active constituent of the proposed agent comprises the reaction product of $H_2O_2$ and metallic titanium, said reaction product being in the form of a gel including a titanium peroxy radical and titanium peroxide, together with titanium hydroxide as important components in its structure.

Although the agent according to the invention has a wide range of anti-inflammatory applications, and various applications will also be described, the invention will be described in the following with reference to a specific area of application without, however, being limited thereto.

It is well known that titanium is particularly suited for implantation in living tissue. One such application has been developed by Professor Branemark in Gothenburg and relates to the implantation of titanium screws into the jaw bone, the implanted titanium screws then serving as anchorage points for artificial teeth. Properties such as surface energy, dielectric constant, corrosion resistance, $pK_a$ and degree of hydration, of the oxide layer on the titanium surface of these screws have been considered important for osseo-integration although their significance has not been conclusively proven. However, it has been proven that the phenomena appearing during the period immediately after implantation are of the utmost importance in establishing biointegration. During this period the inevitable inflammatory reaction caused by the surgical trauma must heal suitably. The initial inflammatory reaction to the implant is characterised by the presence of cells which neutralize and degrade foreign objects. These cells (polymorphonuclear leukocytes and macrophages) are characterised by their ability to produce tissue-degrading enzymes, free oxygen radicals and $H_2O_2$ and engulf foreign particles. Clinical experiments have shown that some of the oxygen radicals produced are extremely dangerous to living tissue; they may attack metals and participate in the production of biologically active mediators.

The object of the agent according to the invention is to achieve wide-spread inhibition of these conditions around such implant bodies, thus considerably shortening the healing period required.

Another object of the invention is to provide a multi-purpose anti-inflammatory agent and an oxidizing agent, particularly a biocompatible oxidizing agent, as well as an agent suitable for cell cultivation, and an agent for treating other inflammatory conditions, such as arthritis.

When using the agent according to the invention for, any kind of implant, the gel is spread on the implant after manufacture and the implant is then stored in the gel until the moment of use. The implant is then cleaned and disinfected and its gel coating inhibits acute inflammation which inevitably occurs when tissue is incised. The implant bodies should of course be kept in suitable containers to avoid degradation due to reduction of the gel.

The gel-like product according to the invention offers optimal properties thanks to its double-oxidizing effect, i.e. by means of both the radical and $H_2O_2$.

The gel proposed according to the invention decomposes in two stages as follows:

$$Ti(IV)O_2^- + e^- \rightarrow Ti(IV)O_2^{2-}$$

$$Ti(IV)O_2^{2-} + 2H^+ \rightarrow Ti(IV)(OH^-)x + H_2O_2$$

The Ti-peroxy radical ($Ti(IV)O_2^-$) has approximately the same redox-potential as $H_2O_2$.

The agent according to the invention can also be used to inhibit skin inflammation, in which case it may be diluted to a suitable concentration with water, or incorporated in ointment bases, etc.

The agent according to the invention is suitably produced by incubating metallic titanium in hydrogen peroxide to form said reaction product.

Metallic titanium is suitably immersed in a 1–30% $H_2O_2$ solution and, when the solution has ceased to give off oxygen, the gel formed is removed and stored in nonreducing environment. The reaction time is approximately two weeks but is of course dependent on the ratio of titanium surface to $H_2O_2$. The pH value should be maintained between 1.3 and 4 during the process.

According to a preferred embodiment of the invention the gel-like final product is dehydrated, suitably at a temperature not exceeding 200° C., and converted to powder form.

The produce according to the invention may suitably be used as a multi-purpose anti-inflammatory agent, such as an oxidant, particularly as a biocompatible oxidant and even for cell cultivation, etc.

The invention will be described in more detail with reference to the following examples.

EXAMPLE I

Metallic titanium was immersed in a 1–30% $H_2O_2$ solution in a vessel. When oxygen production had ceased, the peroxy gel formed in the solution after a reaction time of approximately two weeks (bulk formation) was removed and stored in a non-reducing environment in refrigerated glass containers. The reaction time is of course dependent on the ratio between titanium surface and $H_2O_2$.

The reaction occurs within a pH interval of 1.3–6, preferably pH value 4, and the gel is formed without intermediary steps. Under these conditions the $H_2O_2$ and $O_2$ will react with titanium (III) or titanium (IV) ions leaching out at the oxidized surface. A catalytic decomposition of peroxides, i.e. hydrogen peroxide and titanium peroxide, occurs at the surface. When the peroxides have been decomposed the solution forms a gel at pH value 3 or above.

The transparent, yellowish-green gel thus obtained is free from salts and vital elements of the polymeric structure are

| $Ti(IV)O_2^{2-}$ | and $Ti(IV)O_2^{-}$ |
|---|---|
| (titanium peroxide) | (titanium peroxy radical) |

The gel thus produced has been found to be free from other complexing ions such as sulphate ions, chloride ions, etc. The gel is decomposed through chemical reduction to hydrogen peroxide and titanium hydroxide. In principle the gel thus acts as a slow-release hydrogen peroxide reservoir.

At high concentrations the gel has been found to have bactericidal properties in peroxidase (enzyme) halogen systems and at low concentrations it acts instead, through oxidization and the release of hydrogen peroxide, as an inhibitant against inflammatory activity. The gel also has an anti-inflammatory effect since inflammatory cells adhere to its surface.

The gel produced as described above has also exhibited an ability to oxidize thiol groups, which are important constituents in receptors for complement activation, for instance.

In preliminary tests on white corpuscles from humans and rats this titanium gel was found to influence them in the following manner:

The cells adhere to the surface of the gel without being activated, during the binding process. The gel is nontoxic with respect to the cells and these show normal viability. The gel inhibits phagocytosis (opsonized zymosan) and in the presence of the gel a decrease in oxygen radicals, measured as IL1, (IL1=Interleukin 1) can be shown when the cells are stimulated with opsonized zymosan and immune complexes.

When the gel produced according to the invention was injected into the knee joint of a rabbit, no changes visible through a light microscope could be observed after 6 hours. This indicates that the gel per se does not give rise to inflammation or tissue damage.

The preliminary observations in test tubes and experimental animals described above imply that the gel according to the invention would also possess favourable properties when used in medical context. These properties indicate that it can probably be used against inflammatory processes, for disinfection purposes, to accelerate integration of implants and possibly also accelerate the healing process in other wounds.

EXAMPLE II

A titanium screw for implantation in a jaw bone was immersed in a 0.1-30% solution of hydrogen peroxide, thus initiating leaching of titanium ions out into the surrounding solution. In the catalytic system these ions form titanium peroxide and titanium peroxy radicals. When hydrogen and titanium peroxide are catalytically decomposed, a titanium peroxy gel is produced as the final product. This gel possesses per se anti-inflammatory properties as described above, but it also protects the implant body provided it has not been exposed to contaminated air. The implant is thus also disinfected since the hydrogen peroxide solution is itself bactericidal. Its encapsulation in the gel also ensures that the titanium body is hydrophillic, free from carbon impurities and has a surface that is saturated with respect to hydrated titanium dioxide. This means that, in a pure water solution, the titanium body will not leach out more titanium ions before those already present are transported away. When such a body is implanted, its surface should be coated with the titanium peroxy gel, thus protecting it from external contamination and forming an anti-inflammatory gel between tissue and implant surface. Thanks to the oxidizing action of the titanium peroxy radicals in this gel, as well as the decomposition product—hydrogen peroxide—in cooperation with the peroxidase-halogen system, inflammation is suppressed in the acute stage. Preliminary experiments indicate that when titanium surfaces treated in accordance with the invention are used the integration and healing process is superior to when untreated titanium surfaces are used.

Alternatively, prostheses with titanium surfaces have been incubated in hydrogen peroxide solution of up to 30% to form the claimed agent on the titanium surfaces, in order to achieve cleaning, disinfection and saturation of the oxide layer with respect to hydrated titanium oxide. The agent according to the invention can of course be used for implants of materials other than titanium.

We claim:

1. An anti-inflammatory oxidizing agent, consisting of an active constituent the reaction product of $H_2O_2$ and metallic titanium, said reaction product being in the form of a gel including a Ti-peroxy radical and titanium peroxide, together with titanium hydroxide.

2. The agent as claimed in claim 1, wherein the Ti-peroxy radical is $Ti(IV)O_2$).

3. The agent as claimed in claim 1, wherein the reaction product is in the form of a dehydrated gel.

4. A method for treating inflammation, comprising administering the agent of claim 1 to inflamed tissue.

5. A method for oxidizing a biological substrate, comprising contacting the compound with the agent of claim 1.

6. A method for cultivating a cell comprising contacting the cell with the agent of claim 1.

7. An anti-inflammatory oxidizing composition, consisting: 1) the reaction product of $H_2O_2$ and metallic titanium, said reaction product being in the form of a gel comprising a Ti-peroxy radical, titanium peroxide, and titanium-hydroxide; and 2) a pharmaceutically acceptable carrier.

8. The composition of claim 7, wherein the Ti-peroxy radical is $Ti(IV)O_2^{-}$.

9. The composition of claim 7, wherein the gel is a dehydrated gel.

10. The composition of claim 7, wherein the carrier comprises a water base or an ointment base.

* * * * *